United States Patent [19]

Reyes et al.

[11] Patent Number: 5,218,099

[45] Date of Patent: Jun. 8, 1993

[54] POST-TRANSFUSION, NON-A, NON-B HEPATITIS VIRUS POLYNUCLEOTIDES

[75] Inventors: Gregory R. Reyes, Palo Alto, Calif.; Daniel W. Bradley, Lawrenceville, Ga.; Linda Rabin, Redwood City; Kirk Fry, Palo Alto, both of Calif.

[73] Assignees: The United States of America as represented by the Department of Health and Human Services, Washington, D.C.; Genelabs Incorporated, Redwood City, Calif.

[21] Appl. No.: 372,711

[22] Filed: Jun. 28, 1989

Related U.S. Application Data

[63] Continuation-in-part of Ser. No. 350,570, May 11, 1989, abandoned, which is a continuation-in-part of Ser. No. 334,701, Apr. 6, 1989, abandoned, which is a continuation-in-part of Ser. No. 228,334, Aug. 4, 1988, which is a continuation-in-part of Ser. No. 215,728, Jul. 6, 1988, abandoned, which is a continuation-in-part of Ser. No. 846,757, Apr. 1, 1986, abandoned.

[51] Int. Cl.$^5$ .................. C12N 15/51; C12N 7/00; C12Q 1/70
[52] U.S. Cl. ..................... 536/23.72; 435/5; 435/235.1; 935/9
[58] Field of Search ............. 536/27; 435/235.1, 69.1, 435/69.3, 172.3, 5; 935/9, 12

[56] References Cited

U.S. PATENT DOCUMENTS

| | | | |
|---|---|---|---|
| 4,464,474 | 8/1984 | Coursaget et al. | 436/513 |
| 4,542,016 | 9/1985 | Trepo | 424/86 |
| 4,673,634 | 3/1985 | Seto et al. | 435/5 |
| 4,683,194 | 7/1987 | Saiki et al. | 435/6 |
| 4,683,195 | 7/1987 | Mullis et al. | 435/6 |
| 4,683,202 | 7/1987 | Mullis | 435/91 |
| 4,702,909 | 4/1984 | Villarejos et al. | 424/89 |
| 4,707,439 | 11/1987 | Seto et al. | 435/5 |
| 4,870,026 | 9/1989 | Wands et al. | 436/548 |
| 5,032,511 | 7/1991 | Takahashi et al. | 435/69.1 |

FOREIGN PATENT DOCUMENTS

| | | |
|---|---|---|
| 0154392A2 | 9/1985 | European Pat. Off. . |
| 0186526A1 | 10/1985 | European Pat. Off. . |
| 0190972A2 | 1/1986 | European Pat. Off. . |
| 0263761A2 | 10/1987 | European Pat. Off. . |
| 0293274A1 | 11/1988 | European Pat. Off. . |
| 3316464A1 | 11/1984 | Fed. Rep. of Germany . |
| 2606515 | 5/1988 | France . |
| 61-56196 | 3/1986 | Japan . |
| 62-181798 | 8/1987 | Japan . |
| WO87/05930 | 10/1987 | PCT Int'l Appl. . |

OTHER PUBLICATIONS

Johnson, B. J. B. et al. 1986, *J. Gen. Virol.* vol. 67, pp. 1951–1960.
Muesing, M. A. et al. 1985, *Nature* vol. 313, pp. 450–458.
Young, R. A. et al. 1983, *Proc. Nat. Acad. Sci, USA*, vol. 80, pp. 1194–1198.
Choo, Q. L. et al, 1989, *Science*, vol. 244, pp. 359–362.
"Cloning and Sequencing of the Non-A, Non-B Hepatitis Viral Genome, and use of the DNA in Diagnosis and Vaccine Preparation," Seelig, Renate et al., Chemical Abstracts, vol. 110, (1989), p. 211.
"Cloning of Blood-Borne Non-A Non-B Hepatitis Virus," Armia, Terukatsu, Chemical Abstracts, vol. 111, (Jul. 17, 1989), p. 139.
"Isolation and Functional Property of MRNA Coding for Hepatitis A,B and Non-A-Non-B Viral Particles from Human Sera," A. A. Hakim, Naturwissenschaften, 73 (1986), pp. 45–47.

(List continued on next page.)

Primary Examiner—Richard A. Schwartz
Assistant Examiner—Mary E. Mosher
Attorney, Agent, or Firm—Cooley Godward Castro Huddleson & Tatum

[57] ABSTRACT

Purified virus particles, antigens, antibodies reactive with viral antigens, and a viral genetic material associated with non-A, non-B hepatitis are provided by the present invention. Cloned genetic material useful both in identifying intact virus particles of the invention and for use in diagnostic techniques and/or production of antigens is also disclosed.

11 Claims, 7 Drawing Sheets

OTHER PUBLICATIONS

"Non-A, Non-B Hepatitis Agent," Miyamura, Tatsuo, (Kokuritsu Yobo Eisei *Kenkyusho*, Tokyo, Japan, 141.), *Chemical Abstracts*, vol. 103, (1985), p. 457.

"Biophysical Properties and Morphology of Purified Antigen Associated with Non-A, Non-B Hepatitis," Spertini, O, Frei, P. C., *Chemical Abstracts*, vol. 105, p. 485.

"An Assay for Circulating Antibodies to a Major Etiologic Virus of Human Non-A, Non-B Hepatitis," G. Kuo et al., *Science*, vol. 244, (Apr. 21, 1989), pp. 362–364.

Bradley et al., *Journal of Infectious Diseases*, (Aug. 1983) 148:254–265.

Prince et al., *The Lancet*, (1984) 10:1071–1075.

Bradley et al., *Proceedings of the Third International Symposium on Viral Hepatitis* (Szmuness W., Alter H. J., Maynard J. E. eds. Viral Hepatitis, 1981 International Symposium) (1982) 319–329.

Bradley et al., *Journal of Medical Virology* (1979) 3:253–269.

Bradley, *Journal of Virological Methods* (1985) 10:307–319.

Shimizu et al., *Proc. Natl. Acad. Sci. USA* (1985) 82:2138–2142.

Seto et al., *The Lancet*, Oct. 27, 1984, pp. 941–943.

Seto and Gerety, *Proc. Natl. Acad. Sci. USA* (1985) 82:4934–4938.

```
      E   V   T   G   L   V   Y   N   D   K   D   I   E   N
  1   GAAGTAACAGGACTCGTCTATAACGATAAAGATATCGAAAAT                42

V   V   I   Y   T   A   N   I   Q   K   A   N   V   T
 43   GTTGTTATCTATACGGCTAATATTCAAAAGGCGAATGTGACA                84

Y   I   D   D   T   T   G   K   T   L   E   T   H   G
 85   TACATTGATGACACAACTGGTAAAACTTTAGAGACACATGGA               126

L   S   G   K   T   G   T   T   D   S   Y   K   T   S
127   TTATCAGGTAAGACAGGAACAACAGATAGTTATAAGACTAGT               168

D   T   I   T   S   Y   E   D   K   G   Y   A   L   V
169   GATACGATCACATCTTATGAAGATAAGGGTTATGCATTAGTC               210

S   D   N   Y   P   A   D   G   V   V   Y   D   N   D
211   AGTGATAACTATCCAGCGGATGGAGTTGTGTATGATAATGAT               252

D   A   V   D   Q   N   F   E   V   H   L   K   H   T
253   GACGCTGTTGATCAAAACTTTGAAGTACATTTGAAACATACA               294

T   T   T   V   N   P   K   D   P   Q   T   P   G   E
295   ACAACCACAGTTAATCCAAAGGACCCACAAACACCAGGGGAA               336

P   I   N   P   K   D   P   D   G   P   K   W   P   T
337   CCTATCAATCCGAAGGATCCAGATGGACCAAAGTGGCCAACG               378

G   T   D   A   D   S   L   T   E   T   V   N   E   T
379   GGAACTGATGCTGACTCGTTAACAGAAACTGTTAATGAGACC               420

T   H   Y
421   ACTCATTAT                                                429
```

FIG. 1

```
      T   Q   P   N   S   W   F   Q   R   Q   P   E   T   K
  1 ACACAACCAAATTCTTGGTTCCAGCGCCAACCTGAAACCAAA              42

K   V   A   N   I   A   G   Q   A   S   I   A   S   T
 43 AAAGTGGCAAATATTGCCGGGCAAGCGTCGATTGCTTCGACC              84

A   Y   V   S   Q   D   A   A   I   S   A   Y   N   K
 85 GCCTATGTGAGCCAAGATGCGGCCATTTCGGCCTACAATAAA             126

V   K   N   A   V   V   T   V   Q   N   L   Q   K   N
127 GTAAAAAATGCTGTGGTCACCGTGCAAAACTTGCAAAAGAAT             168

A   A   Q   T   P   D   G   F   A   G   L   F   G   Q
169 GCGGCCCAAACCCCAGATGGTTTTGCGGGGTTGTTTGGTCAA             210

S   G   R   Q   K   Q   A   D   N   N   G   Q   V   E
211 TCAGGGCGTCAAAAGCAAGCCGATAATAATGGCCAAGTTGAA             252

T   A   S   E   G   S
253 ACTGCCTCAGAAGGCTCT                                     270
```

FIG. 2

```
        K   N   N   K   I   L   H   L   R   K   S   A   T   K
  1   AAAAATAACAAGATCTTACATTTACGGAAATCTGCGACAAAA      42

V   S   K   Y   K   I   K   K   L   S   V   G   V   A
 43   GTTTCCAAATATAAGATCAAAAGTTAAGTGTTGGTGTCGCC        84

S   V   L   V   G   A   T   F   F   L   G   S   T   A
 85   TCCGTTCTGGTGGGGGCCACTTTCTTCCTTGGTTCGACAGCG      126

S   A   S   A   S   D   E   Q   L   A   D   K   Q   A
127   AGTGCAAGTGCTTCTGATGAGCAACTCGCTGATAAGCAGGCA      168

G   V   T   Q   Q   T   D   Q   N   A   T   N   T   N
169   GGGGTCACACAACAAACTGATCAAAATGCAACAAACACAAAT      210

D   R   V   L   K   F   D   M   A   T   S   T   A   T
211   GATCGGGTATTAAAGTTTGACAATGCAACGTCAACGGCCACA      252

T   D   N   A   D   S   S   A   A   K   M   S   N   V
253   ACGGATAATGCTGATTCTAGTGCGGCCAAAATGTCAAACGTT      294

A   Q   A   D   N   S   A   N   N   A   T   V   A   N
295   GCGCAAGCTGACAATTCAGCCAACAATGCAACAGTAGCTAAT      336

N   L   D   K   K   S   I   T   D   S   T   L   S   N
337   AATCTTGATAAAAAATCAATTACCGATTCTACATTATCCAAT      378

N   N   D   L   K   S   T   E   M   Q   S   T   V   T
379   AATAACGATTTAAAATCAACTGAAATGCAATCAACTGTTACT      420

D   Q   A   A   A   D   D   A   S   T   A   D   Q   T
421   GACCAAGCAGCAGCTGACGATGCAAGTACTGCTGATCAAACA      462

A   T   E   K   Q   A   T   V   T   N   Q   A   T   V
463   GCAACTGAAAAGCAAGCAACTGTGACCAATCAAGCCACAGTT      504

D   N   T   V   N   T   A   D   Q   A   T   Q   A   A
505   GATAACACAGTAAATACTGCTGACCAAGCAACTCAAGCAGCA      546

A   E   K   T   T   T   P   A   S   T   A   A   N   T
547   GCTGAAAAGACAACAACGCCTGCAAGTACTGCTGCCAACACG      588

Q   A   A   A   L   V   A   T   L   R   A   A   A   T
589   CAAGCAGCTGCACTAGTTGCAACGCTACGTGCCGCAGCAACT      630

A   D   T   S   T   T   T   T   V   N   N   W   T
631   GCGGATACAAGTACGACGACAACTGTTAACAACTGGACT          669
```

FIG. 3

```
      P   S   A   S   I   Q   E   A   M   D   K   Q   L   T
  1 CCATCGGCTTCCATCCAGGAAGCAATGGATAAGCAGTTAACG    42

A   D   R   E   R   V   A   T   I   A   K   A   E   G
 43 GCTGATCGTGAACGAGTGGCAACTATTGCAAAAGCCGAAGGG    84

E   A   R   S   I   E   L   T   T   K   A   K   N   D
 85 GAGGCACGCTCCATCGAACTCACAACCAAGGCTAAAAATGAC   126

A   L   M   A   T   A   K   A   E   A   D   A   T   K
127 GCGTTGATGGCGACGGCGAAAGCCGAAGCTGACGCGACGAAA   168

T   R   A   D   A   E   R   Y   R   I   D   T   V   Q
169 ACCCGTGCTGATGCCGAACGTTACCGAATCGATACGGTACAA   210

A   G   L   A   G   A   D   D   K   Y   F   Q   N   Q
211 GCTGGTTTGGCTGGGGCGGATGACAAGTACTTCCAAAACCAA   252

S   I   N   A   F   A   T   L   A   N
253 TCCATTAACGCATTCGCGACGTTACCCAAT              282
```

FIG. 4

Sequence 1: clone 385-11-5

```
            ATCGAGAGCAACGCACTGGCAGTGTCCAACCTGGATTTCTGATC
CTGTTTTGACCCGCAGTACCCAAAAAGGCCAACGCTCAGCGTTGGCCTTT
TTTAATGGCTAAAAAATGACTATGGCGCCAACAGCACCGCCCTCTCCTCG
CGGCACAACTCCAGTAAAAAATCCCACACCACCCTCAACCTTACGGATTT
GTGCAGTTCCCGGCGGGTGCTGATCCAGTAACTGCGTTGCACAGACTCGC
CCGGCAATACACGCACCAGGTCGGGGTCGTCAGCGGCCATGTAGTTGGGC
AATACGGCGATACCCAGGCCGGCGCGAGCGGCTTGTTGCTGGGCAATGAC
GCTGGTGCTGCGAAAGGTCACGGTCGGGGTGCGGCAGAAGGTATTGAGGA
ACAGCAGCTCCTGACTGAACAACAGGTCGTCGACGTAGCCGATCCAGTAG
TGGTTGCCA
```

Sequence 2: clone 385-16-2

```
                  GTCATCACGCACAACAGGGGTGTTGAGCGGTGC
ACCGAGTTCTTTCCAGTCCGGGAACAATTCGTTCAGCGCACGGGGTTCAA
ACACGGCACCGGACAGGATGTGAGCGCCGACTTCGGAGCCTTTTTCGACC
ACGCAGACGCTGATTTCCTTACCGGCTTCGGCGGCCTTCTGCTTCAATCG
GCAGGCGGCAGACAGGCCTGCCGGGCCAGCGCCGACGATGACCACGTC
```

FIG. 5-1

Sequence 3: clone 385-2-14

```
                        GTTGACCACTCCCTGGCCGTCGAAGCCGGTG
GTTCGACCGACGCCTTCGAGAAGAACCGCGCCATCGAAGACCGCCGCAAC
GAAGACTGTTTCCACTTTATCGAGTGGACCAAAAAGGCCTTCAAGAACGT
CGATGTGATCCGCCGGGCAACGGCATCATGCACCAGATCAACCTGGAGAA
AATGTCGCCGGTGATCCAGGTGCGCGACGGCGTAGCTTCCGGATACCTGC
GTCGGCACCGATAGCCACACGCCCACGTGGATGCCTTGGCGTGATCGCAT
CGGCTCTGGCGCGTA
```

Sequence 4: clone 385-20-1

```
                      CCCCATAGAGCCCGGACCCATAGACAGCCCTG
CCCCATAGACAGTCTGGCCCTATAGACAGCCCAGCCCCATAGAGCCCGGC
CCTATAGATAGCCCGGCCCCATACAGCCCGGACCCATAGAGAGCACTGCC
CCATAGAGCCCGGACCCATAGAGCCCTGCCCCATAGACAGTC
```

Sequence 5: clone 386-8-1

```
                        GCCAAAGAGTGGCGCACCGACCGTTCCCTCAG
CCGCCTCGAAGCCATGCTCGCCGTGGCCAACAAAGACGCCTCCCTGATCA
TCACCGGCAACGGTGACGTGGTAGAGCCAGAAAACGGCTTGATCGCCATG
GGCTCCGGTGGCGGCTACGCCAGGCTGCGGCCAGTGCGCTGTTGAAGAAA
ACCGACCTGTCGGCCCGTGAAATCGTCGAGACCGCCTTGGGCATCGCTGG
CGATATCTGCGTGTTCACCAACCACAACCTGACCATTGAGGAGCAGGACC
TCGCCGAGTAAGCCGTAGGCTTATTC
```

FIG. 5-2

Sequence 6: clone D20

```
                          GGCGATGACGGCTGCACCGCAAGCACCAGTA
TCAGTCCAGCCAAGTGAAACAGTGACACCTGCACAACCCGTCAAAGTTGC
ACCACAAGTGGTTGCAGCGCAACCAACGTCAACACCAACACCAACGGTAA
CAGTTGAGACTGTACCATCAACGCCTACGCCAGTGCCACCAACATTGGCA
ACGCCACCAATTGCACAACCAGTGGTAACTGCTGCGCCAACTGAAGAAGC
AGCCGTTGCCAACCAGTTGTGGGCACGTACGGGACAAAATGCGGTCTTTG
CCGTCCTACAACAAGCGAACGGAGACGCTTAGTCGCGTGAAGGCTGCTTG
GTCAGACTTGATTAGTCAATTTGGTGTTGCTGAACAGGCCTTACTGACGA
TTGCCGCCCAGTAGCTGCAAGTGAGGAAGGGCTTGTTTTAGCGTTTGAT
TTTCCACCTTTATTGGCGCAAGCTTTACAAGATGCCGCCTTGCAAACGCA
ATTACGGACAGCGCTGGCTGCACAACAATTGCCAACAGAAATGGTGTTGA
TTACCCAAGATAGCTGGCAACAAGAACGCTCTGATTATGTCGCGCAGTTA
AAGGCGGGGACGACTCAACCTTTGAATTTGGCGGATATACCGAGAGTGAG
CCAAACAACCACGACCCAGTCGCAAAGTGCACCGACACCAGAGCAAACGG
GGCTTG
```

Sequence 7: clone S14

```
TCGGGCCGGTAATGACCACGGCCACCATAGCACCGCGAAGAAGCCTGCGA
TGGCGACGCTGGAGGCCATGGTGACGACGCTCCAATCGATGTCCGCGCGC
GCTCGGCGGCGCGATCTGCCGGATATCATCCGGCGCACCAGTCGGACGCC
GCAGCCGCGCTACCGGCCCGAGAAAGAAGATCGCCGCCGCCCATTCGATG
GGGAACG
```

FIG. 5-3

POST-TRANSFUSION, NON-A, NON-B HEPATITIS VIRUS POLYNUCLEOTIDES

CROSS-REFERENCE TO RELATED APPLICATIONS

This application is a continuation in part of U.S. application Ser. No. 350,570, filed May 11, 1989, now abandoned, which is a continuation in part of U.S. application Ser. No. 334,701, filed Apr. 6, 1989, now abandoned, which is a continuation in part of U.S. application Ser. No. 228,334, filed Aug. 4, 1988, which is a continuation in part of U.S. application Ser. No. 215,728, filed Jul. 6, 1988, now abandoned, which is a continuation in part of U.S. application, Ser. No. 846,757, filed Apr. 1, 1986, now abandoned.

INTRODUCTION

1. Technical Field

This invention relates to virus associated with post transfusion non-A, non-B (PT-NANB) hepatitis, to PT-NANB antigens produced by recombinant processes, and to products and processes associated with vaccination against, diagnosis of, and prophylaxis of PT-NANB hepatitis.

2. Background

Acute viral hepatitis is a systemic infection with predominant pathology affecting the liver. Five types of viral agents which cause hepatitis are known to exist: hepatitis A virus (HAV), hepatitis B virus (HBV), post transfusion (PT) and enteric transmission (ET), non-A, non-B (NANB) hepatitis agents, and the HBV-associated delta virus. Specific viral agents have been associated with HAV, HBV, and delta virus. However, despite numerous publications reporting agents associated with PT-NANB hepatitis, there does not appear to be any consensus that the etiologic agent has been identified. Harrison's *Principals of Internal Medicine*, 11th edition (1987), reports that there are at least two different blood-borne NANB hepatitis agents, although the virus(es) or virus antigens are said not to have been identified definitively.

Routine screening of blood donors for anti-HBV antibody and HBV antigen (HBsAg) has decreased the incidence of hepatitis B after blood transfusion, but post-transfusion PT hepatitis due to infection with NANB hepatitis agents is still a significant problem because of the lack of an acceptable serologic screening test to identify PT-NANB hepatitis agents. Identification of new viruses and the use of genetic information obtained from the viruses to produce recombinant proteins that are safe for use in vaccines and diagnostics are major goals in the development of a safe blood supply.

RELEVANT LITERATURE

PT-NANB viruses and antigens have been reported. See for example, U.S. Pat. Nos. 4,464,474, and 4,542,016. The PT-NANB virus has been reported to be a togavirus. See, for example, U.S. Pat. No. 4,464,474. Genetic engineering of hepatitis viral genes, identified as hepatitis C virus, is reported in European Patent Application 88310922.5 (publication number 0 318 216 A1).

SUMMARY OF THE INVENTION

In accordance with the subject invention, isolates comprising virus particles associated with PT-NANB hepatitis and genomic material derived therefrom, together with methods for their preparation and use, are provided. The virus particles are characterized as being obtainable from cells susceptible to NANB hepatitis infection in a host infected with NANB hepatitis; capable of inducing NANB hepatitis in a susceptible host; and capable of inducing expression of NANB virus specific antigens in cells susceptible to infection by the virus. The virus particles can be used as a source of genomic material for preparing polynucleotide probes for diagnosis, as well as antigens and vaccines for therapeutic and diagnostic applications. Propagation of the virus particles in vitro can be used to identify virus-specific cell-surface antigens, and as a source of such antigens. Attenuated or inactivated virus particles can be used as vaccines.

BRIEF DESCRIPTION OF THE DRAWINGS

FIG. 1 shows a fragment of PT-NANB virus derived from clone #30. The top line represents the amino acid sequence which is encoded by the nucleotide sequence shown in the lower line.

FIG. 2 shows a fragment of PT-NANB virus derived from λgt-11 clone PT-2. Abbreviations are as for FIG. 1.

FIG. 3 shows a fragment of PT-NANB virus derived from λgt-11 clone PT-8. Abbreviations are as for FIG. 1.

FIG. 4 shows a fragment of PT-NANB virus derived from λgt-11 clone PT-19. Abbreviations are as for FIG. 1.

FIGS. 5-1 to 5-3 show a series of 7 fragments of PT-NANB virus genetic material. Only the cDNA sequences are shown in this Figure.

DESCRIPTION OF THE SPECIFIC EMBODIMENTS

The present invention provides unambiguously identified viral genetic material and a source of virus particles associated with post transfusion non-A, non-B (NANB) hepatitis. The virus particles may be obtained from samples suspected of containing virus particles, such as serum of infected humans and other anthropoid species, by fractionation of the samples based upon buoyuant density and from cells susceptible to infection with NANB virus, such as hepatocytes. The virus particle isolates may be used directly as a source of genomic material for preparing probes for diagnosis, antigens and vaccines for therapeutic and diagnostic purposes, or they may be propagated in a susceptible cell line such as a trioma comprising human hepatocytes. The infected cells may be used either as a source of virus particles or may be used for identifying NANB virus specific antibodies or antigens, and as a source of such antigens.

Viral particles can be obtained from an infected human or other infected source such as a chimpanzee, from plasma, or from other cells susceptible to infection by NANB virus, such as the hepatocyte. To obtain viral genomic material, the biological sample can be centrifuged and viral RNA extracted from viral particles in the sample. Alternatively, a purified fraction comprising viral particles may be obtained by fractionation of the sample on a density gradient, such as a sucrose density gradient. Fractions having a buoyant density of from about 1.07 to about 1.13 gm/cm$^3$, preferably 1.09 to 1.11 gm/cm$^3$ are collected. Fractions comprising the virus particles can then be extracted and cDNA clones prepared from the viral RNA. The virus may be further characterized as having a genome comprising RNA sequences which may be reverse transcribed to obtain at least one of the cDNA sequences shown in FIGS. 1-5. All of these sequences are derived from viral genetic material isolated from humans or chimpanzees infected with PT NANB. For example, the first five sequences shown in FIG. 5 are derived from virus obtained from humans. These sequences are derived from different segments of the viral genome and appear to be unrelated. The last two sequences shown in FIG. 5 are derived from virus obtained from infected chimpanzees. All of these sequences appear to be different from previously known NANB sequences, such as those disclosed in published European application 0 318 216 A1, which was mentioned above as identifying hepatitis C viral segments.

Any sequence of nucleotides from the above sequences may be used as a probe or primer for detecting or regulating the viral nucleic acid. Such probes can be considerably shorter than the entire sequence but should be at least 16 nucleotides in length. Intermediate oligonucleotides from 20 to 500, especially 30 to 200, nucleotides in length provide particularly specific and rapid-acting probes. Longer oligonucleotides are also useful, up to the full length of a gene. Both RNA and DNA probes may be used. In addition, an at least 8, usually at least 12 amino acid sequence, conveniently at least a 20-amino acid sequence, may be employed as an epitopic site, an immunodominant sequence, a hapten or the like for the production of diagnostic reagents, vaccines, production of antibodies, isolation of antibodies from serum or the like. Usually, the isolated peptide will be fewer than about 125 amino acids, frequently fewer than about 100 amino acids. Amphipathic sequences or sequences fulfilling the Rothbard algorithm may be used, as exemplified by G-V-V-Y-D-N-D-D, or E-P-V-N-P-K-D-P.

Sequences homologous with the viral sequences should hybridize and be detectable under the conditions described for detecting/hybridizing RNA in Maniatis et al., *Molecular Cloning, A Laboratory Manual*, Cold Spring Harbor Laboratory, Cold Spring Harbor, N.Y., 1982, p. 332. See also, pages 324-328 for DNA hybridization conditions, particularly paragraph 6, p. 325.

Since significant sequences of genetic material (as cDNA) have been fully identified, it is possible to produce a variety of DNA and RNA sequences based on this natural sequence partially or entirely by synthetic chemistry, after which the sequences obtained can be inserted into any of the many available DNA vectors using known techniques of recombinant DNA technology. Thus the present invention can be carried out using reagents, plasmids, and microorganism which are freely available and in the public domain at the time of filing of this patent application.

For example, nucleotide sequences greater than 100 nucleotides in length can be readily synthesized on an Applied Biosystems Model 380A DNA Synthesizer as evidenced by commercial advertising of the same (e.g., *Genetic Engineering News*, November/December 1984, p. 3). Such oligonucleotides can readily be spliced using, among others, the technique of preparing overlapping complementary sequences (e.g., 1-100 of coding strand, 0-50 and 51-150 of complementary strand, 101-200 of coding strand, etc.) followed by hybridizing and ligating the strands.

Furthermore, automated equipment is also available that makes direct synthesis of any of the peptides disclosed herein readily available. In the same issue of *Genetic Engineering News* mentioned above, a commercially available automated peptide synthesizer having a coupling efficiency exceeding 99% is advertised (page 34). Such equipment provides ready access to the peptides of the invention, either by direct synthesis or by synthesis of a series of fragments that can be coupled using other known techniques.

In addition to the specific polypeptide sequences shown in FIGS. 1 to 5, peptide fragments based on these sequences and fragments representing minor variations thereof will have the biological activity of the various peptides. For example, fragments of the given peptide sequence that are capable of being recognized by immunoglobulins specific for NANB hepatitis can readily be prepared and screened. Peptide synthesizers can be used to prepare small polypeptide fragments (e.g., less than 100 amino acids) or techniques of genetic engineering can be used to prepare larger fragments. A simple screening procedure that will identify suitable polypeptide fragments consists of preparing monoclonal antibodies to an entire encoded antigen, attaching the antibodies to an affinity column, and capturing peptide fragments that are retained by the bound antibody. Polyclonal antisera can be used instead of monoclonal antibodies if desired. The suitability of this technique has been demonstrated experimentally.

The ability to prepare and select appropriate immunologically active fragments from a larger protein is well known in the art and is described in a number of publications, including patents. See, for example, U.S. Pat. No. 4,629,783, which describes the preparation of immunologically active fragments of viral proteins. One common variation is the preparation of a polypeptide of the invention in the form of a fused polypeptide. Such peptides are typically prepared by using the promoter region of a gene known to be expressed in a host and inserting nucleotides that encode all or a major portion of the amino acid sequence of the invention into the genetic sequence for the host protein. Examples of such fused proteins include the $\beta$-galactosidase fused protein discussed below.

Another technique for preparing immunologically active peptide fragments is to synthesize a series of amino acids of from 5-100 amino acids in length (or any intervening length, such as 10, 15, or any other multiple of 2, 3, or 5 in this range) and screen for immunological activity using an antiserum (or monoclonal antibody). The fragments are selected along the entire length of the peptide to optimize cross-reactivity (e.g., a series of peptides 20 amino acids in length and comprising $AA_1$-$AA_{20}$, $AA_5$-$AA_{25}$, $AA_{10}$-$AA_{30}$, etc.). The selected fragment then corresponds to particularly useful corresponding nucleotide sequences that can be used to produce large amounts of the peptide by recombinant techniques, for use as described herein.

In addition, minor variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, a cysteine with a serine or alanine, or a similar replacement of an amino acid with a structurally related amino acid (i.e., a conservative replacement) will not have a major effect on the biological activity of the resulting molecule, especially if the replacement does not involve an amino acid at a binding site or other site of biologic activity. Whether a change results in a functioning peptide can readily be determined by direct analysis for function in an immunization or in a diagnostic test that relies on immunogenic specificity. Examples of this process are described later in detail. Peptides in which more than one replacement has taken place can readily be tested in the same manner. Preferred peptides differ at no more than 12, more preferably no more than 5, amino acids in any contiguous group of 20 amino acids. Standard conservative groups of amino acids are shown in parenthesis using the one-letter amino acid code: nonpolar (A,V,L,I,P,M); aromatic (F,T,W); uncharged polar (G,S,T,C,N,Q); acidic (D,E); basic (K,R,H). The aromatic groups are sometimes considered to belong to the broader-defined nonpolar (F,W) or uncharged polar (T) groups.

Other DNA molecules that code for such peptides can readily be determined from the list of codons in Table 1 and are likewise contemplated as being equivalent to the DNA sequences of FIGS. 1 to 5. Since there is a fixed relationship between DNA codons and amino acids in a peptide, any discussion in this application of a replacement or other change in a peptide is equally applicable to the corresponding DNA sequence or to the DNA molecule, recombinant vector, or transformed microorganism in which the sequence is located (and vice versa).

TABLE 1

The Genetic Code[1]

| First Position (5' end) | Second Position U | C | A | G | Third Position (3' end) |
|---|---|---|---|---|---|
| U | PHE | SER | TYR | CYS | U |
| | PHE | SER | TYR | CYS | C |
| | LEU | SER | Stop | Stop | A |
| | LEU | SER | Stop | TRP | G |
| C | LEU | PRO | HIS | ARG | U |
| | LEU | PRO | HIS | ARG | C |
| | LEU | PRO | GLN | ARG | A |
| | LEU | PRO | GLN | ARG | G |
| A | ILE | THR | ASN | SER | U |
| | ILE | THR | ASN | SER | C |
| | ILE | THR | LYS | ARG | A |
| | MET | THR | LYS | ARG | G |
| G | VAL | ALA | ASP | GLY | U |
| | VAL | ALA | ASP | GLY | C |
| | VAL | ALA | GLU | GLY | A |
| | VAL | ALA | GLU | GLY | G |

[1]Given the position of the bases in a codon, it is possible to find the corresponding amino acid. For example, the codon (5')AUG(3') on mRNA specifies methionine, whereas CAU specifies histidine. UUA, UAG, and UGA are termination signals. AUG is part of the initiation signal, and it codes for internal methionines as well.

In addition to the specific nucleotide sequences listed in FIGS. 1 to 5, DNA (or corresponding RNA) molecules of the invention can have additional nucleotides preceding or following those that are specifically listed. For example, poly A can be added to the 3'-terminus of the cDNA, a short (e.g., fewer than 20 nucleotides) sequence can be added to either terminus to provide a terminal sequence corresponding to a restriction endonuclease site, stop codons can follow the peptide sequence to terminate translation, and the like. Additionally, DNA molecules containing a promoter region or other control region upstream from the gene can be prepared. All DNA molecules containing the sequences of the invention will be useful for at least one purpose since all can minimally be fragmented to produce oligonucleotide probes and be used in the isolation or detection of PT NANB specific nucleic acid sequences from biological sources.

Peptides of the invention can be prepared for the first time as homogeneous preparations, either by direct synthesis or by using a cloned gene or a fragment thereof as described herein. By "homogeneous" is meant, when referring to a peptide or DNA sequence, that the primary molecular structure (i.e., the sequence of amino acids or nucleotides) of substantially all molecules present in the composition under consideration is identical. The term "substantially" as used in the preceding sentence preferably means at least 95% by weight, more preferably at least 99% by weight, and most preferably at least 99.8% by weight. The presence of fragments derived from entire molecules of the homogeneous peptide or DNA sequence, if present in no more than 5% by weight, preferably 1% by weight, and more preferably 0.2% by weight, is not to be considered in determining homogeneity since the term "homogeneous" relates to the presence of entire molecules (and fragments thereof) that have a single defined structure as opposed to mixtures in which several molecules of similar molecular weight are present but which differ in their primary molecular structure.

The term "isolated" as used herein refers to pure peptide, DNA, or RNA separated from other peptides, DNAs, or RNAs, respectively, and being found in the presence of (if anything) only a solvent, buffer, ion or other component normally present in a biochemical solution of the same. "Isolated" does not encompass either natural materials in their native state or natural materials that have been separated into components (e.g., in an acrylamide gel) but which have not been obtained either as pure substances or as solutions. The term "pure" as used herein preferably has the same numerical limits as "substantially" immediately above. The phrase "replaced by" or "replacement" as used herein does not necessarily refer to any action that must take place but to the peptide that exists when an indicated "replacement" amino acid is present in the same position as the amino acid indicated to be present in a different formula.

Salts of any of the biological molecules described herein will naturally occur when such molecules are present in (or isolated from) aqueous solutions of various pHs. All salts of molecules having the indicated biological activity are considered to be within the scope of the present invention. Examples of salts that can occur with peptides include alkali, alkaline earth, and other metal salts of carboxylic acid residues, acid addition salts (e.g., HCl) of amino residues, and zwitterions formed by reactions between carboxylic acid and amino residues within the same molecule.

The invention specifically contemplates each and every possible variation of polynucleotide that could be made by selecting combinations based on the possible codon choices listed in FIGS. 1 to 5 and Table 1, and all such variations are to be considered as having been specifically disclosed. In order to avoid redundancy, such variations are not set forth here.

Although genes and corresponding proteins can be prepared by the totally synthetic techniques discussed above, in preferred embodiments of the invention genetic information is obtained from natural sources and identified as described herein. The genetic material is first obtained in the form of a gene library, using any of numerous existing techniques. The first of these is to randomly shear genomic DNA and insert this sheared material into expression vectors, e.g., λgt11. If enough recombinants are generated, there is a good probability of having at least one recombinant in the population which is expressing a fusion protein corresponding to an antigen of interest. In practice, for a genome the size of the present virus (about 10 kbp, as DNA) at least about $6 \times 10^3$ independent recombinants are needed. This allows for the entire genome to be represented by recombinants with an average insert size of 100 bp where at least one insert will exist with one of its ends falling within any 10-base-pair region. Allowing for only 1 in 6 such insertions being in the correct orientation and reading frame, functional recombinants should exist in such a library with fusions corresponding to approximately every 10 base pairs.

A second strategy for preparing gene libraries is to make complementary DNA (cDNA) copies of the total RNA of the virus and to clone these as recombinant molecules in expression vectors. Use of a cDNA library to obtain genetic information for use in the present invention is preferred. Such a library has been generated from NANB-infected human plasma and screened with serum from a NANB-infected human. Among the recombinants expressing determinants reactive with the serum are those described in FIGS. 1 to 4.

Polyclonal antisera to NANB can be used to screen a cDNA library in order to locate the desired genetic material. cDNA fragments are inserted into an expression vector and after transformation into a suitable host, the host may be screened for proteins which bind to the polyclonal antisera. Recombinants initially identified in this manner can be isolated. The resulting clones may then be used as probes to further search the library for larger fragments or partially overlapping fragments until the complete cDNA is identified.

The NANB genetic material can be used for the production of full fragments or of modified peptides using standard techniques of manipulating and growing unicellular microorganisms. Antigens which are candidates for vaccine development and/or diagnostic reagents will include those recognized by serum from infected patients. Additionally, any of the genetic sequences can be used as probes in hybridization assays.

Although the techniques set forth above, when used in combination with the knowledge of those skilled in the art of genetic engineering and the previously stated guidelines, will enable isolation of the desired genetic material and its use in recombinant DNA vectors in conjunction with the disclosed sequence, other methods which lead to the same result are also known and may be used in the preparation of recombinant DNA vectors of this invention.

Expression of protein, e.g., for use in vaccines, can be enhanced by including multiple copies of the gene in a transformed host, by selecting a vector known to reproduce in the host (such as pUC8; ptac12; pIN-III-ompA1, 2, or 3; pOTS; pAS1; or pKK223-3), thereby producing large quantities of protein from exogenous inserted DNA or by any other known means of enhancing peptide expression. In all cases, a viral protein will be expressed when the DNA sequence is functionally inserted into the vector. By "functionally inserted" is meant in proper reading frame and orientation, as is well understood by those skilled in the art. Typically, a gene will be inserted downstream from a promoter and will be followed by a stop codon, although production as a hybrid protein (possibly followed by cleavage) may be used, if desired.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineered microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering by substitution of a subject sequence for the existing open reading frame sequence.

The implications of the present invention are significant in that unlimited supplies of NANB viral proteins and genetic material of the subject strain will become available for use in the development of hybridization assays or in any other type of assay utilizing these materials as a reagent for use in diagnosis, immunization, therapeutics, and research. Methods of using genetic material in a hybridization assay and equipment for expansion and amplification of genetic material are commercially available in the PCR system (Perkin-Elmer Cetus).

Particularly contemplated is the isolation of genes and viral genomes that can express protein from the subject virus using oligonucleotide probes based on the principal and variant nucleotide sequences disclosed herein. In use, the probes are typically labeled in a detectable manner (e.g., with a radionuclide, e.g., $^{32}P$, $^{3}H$, or with biotin) and are incubated with single-stranded DNA or RNA from the organism in which a sequence is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known. Identity of virus or genetic material obtained from any source with the virus and genetic material of the invention can be confirmed by hybridization assays using probes prepared from the genetic sequences described herein.

Although probes are normally used with a detectable label that allows easy identification, unlabeled oligonucleotides are also useful, both as precursors of labeled probes and for use in methods that provide for direct detection of double-stranded DNA (or DNA/RNA), such as absorption onto nitrocellulose. Accordingly, the term "oligonucleotide probe" refers to both labeled and unlabeled forms.

Additionally, it is possible to purify virus particles from any source and reduce the amount of screening necessary for identifying virus particles and genetic material associated with NANB hepatitis by fractionating, according to buoyant density, biological samples suspected of containing virus, such as a viral pellet obtained from serum or other bodily fluid of an anthropoid infected with NANB hepatitis. By selecting fractions of the proper buoyant density, samples are enriched for the specific virus of the invention. Virtually 100% of a titered inoculum may be recovered from the buoyant density fractions described herein.

Using such techniques, clones have been prepared and characterized as making an immuno-reactive protein recognized by NANB antiserum (a $\beta$-gal fusion product). The genetic material is exogenous to both human and chimpanzee genomes (both infected and uninfected) and, after amplification of the genetic material extracted from buoyant density fractionated serum, is positive for hybridization with a sample obtained from an NANB-infected chimpanzee and negative in the same analysis when tested against amplified genetic material obtained from a control chimpanzee infected with hepatitis B virus.

As a means of propagating relatively large amounts of viral genomic material, viruses of the invention can be cultured in vitro using a hybrid cell line susceptible to infection by the virus. Immortalized virus-specific tissue cells which can be used to culture the NANB viruses of the invention are specifically described in U.S. application Ser. No. 846,757, filed Apr. 1, 1986. Techniques for obtaining virus particles from cell culture are described in the aboveidentified application and in U.S. Pat. No. 4,464,474 which disclosure is hereby incorporated by reference.

The general methods for infecting and culturing the hybrid cells with a selected human infectious virus are as follows: Plasma from a human or other NANB-infected source such as a chimpanzee is used to infect the hybrid cells, and viral infection is followed by monitoring a virus-related cell change over time in culture. NANB virus infection is characterized by the appearance of virus-specific antigens, so the viral infection is properly followed by immunological methods for detecting antigens. After viral infection and propagation, the virus can be isolated, if desired, by conventional means for releasing and purifying virus particles from cells. For example, virus particles may be isolated by lysing the cells and subjecting the lysate to the technique of fractionating samples according to buoyant density, as described below, without additional purification techniques that might disrupt virus particles. The isolated particles will reproduce the virus-related cell change when uninfected hybrid cells are exposed to virus particles.

It may be desirable for a variety of reasons to further purify the particles present in a sample containing particles of the invention. For example, if a virus particle is to be treated and employed as a vaccine or in an immunoassay, there ordinarily should be as little in the way of extraneous protein contamination as possible. Thus, the particle should be substantially free of primate proteins.

NANB viral antigens may be obtained from a variety of sources. The antigen may be present on an intact virus particle, a partially degraded virus particle, a protein- or carbohydrate-containing molecule in solution, or any other physical form, including an antigen that has been combined either chemically or physically with particle or solid surfaces, such as by attaching antigens to the surface of a test tube or to suspended particles, such as red blood cells or latex particles. An antigen of the invention is defined as a substance containing at least one epitopic site of a virus particle.

To obtain NANB viral antigens, the antigens, whether soluble or in some other form, are typically first separated from water insoluble contaminants having greater dimensions or different density than the intact particles, such as animal cells and cell debris and cellular microrganisms, such as bacteria. This gross separation is generally accomplished by low-speed centrifugation or by filtration using standard techniques. Ordinary filters having an average pore diameter of 0.45 microns are useful in retaining gross contamination and passing through the antigens.

Additionally, antigens of the invention may be separated from undesired water-soluble materials after gross contamination is removed. Where it is desired to recover either intact virus particles or their water-insoluble fragments, it is convenient to simply remove all water soluble constituents from the sample. Suitable techniques include ultrafiltration through a membrane, use of selective flocculating or proteinprecipitating agents (such as polyethylene glycol and ammonium sulfate), and chromatography. Chromatography is the most versatile method since it can be readily scaled up for commercial manufacture of antigen. Gel chromatography systems using cross-linked dextran beads are typical of the materials used. A column of a suitable gel can be selected which will permit diffusion of proteins and low molecular weight substances into the void volume of the gel beads, thereby retarding the progress of these contaminants through the column, while allowing whole virus particles to pass through virtually unimpeded. When a particular antigen is desired, other gel sizes can be selected to provide for isolation of an antigen of any particular size. The gel which is selected will thus be a matter of routine experimentation.

Any of the techniques described herein can be combined as desired. For example, isolation of particles on a cesium chloride or sucrose density gradient can be followed by disruption of particles using any of a variety of techniques and isolation of a viral antigen on gel electrophoresis, selecting for proteins binding to antibodies, e.g., antisera, specific for NANB antigens.

One technique that is particularly suitable for isolating soluble protein antigens or particle fragments is affinity chromatography. Antibodies capable of binding antigens of the invention are covalently linked or adsorbed to an insoluble support using conventional procedures. The coupled antibody is placed in a column. A sample containing antigen is passed through the column, where it binds to the coupled antibody. The immunologically-bound antigen is washed with buffer and can then be released by, for example, changing the ionic strength or pH of the wash buffer. Generally, an acidic pH is effective for releasing the bound antigen. The technique is highly effective in separating closely related proteins from the antigens of the invention.

Antigens of the invention can be used as a vaccine. A preferred starting material for preparation of a vaccine is the particle antigens produced by tissue culture of the infectious virus. The antigens are preferably initially recovered as intact particles as described above. However, it is also possible to prepare a suitable vaccine from particles isolated from other sources or non-particle recombinant antigens. When non-particle antigens are used (typically soluble antigens), proteins native to the viral envelope or viral capsid are preferred for use in preparing vaccines. These proteins can be purified by affinity chromatography, also described above.

If the purified protein is not immunogenic per se, it can be bound to a carrier to make the protein immunogenic. Carriers include bovine serum albumin, keyhole limpet hemocyanin and the like. It is desirable, but not necessary to purify antigens to be substantially free of human protein. However, it is more important that the antigens be free of proteins, viruses, and other substances not of human origin that may have been introduced by way of, or contamination of, the nutrient medium, cell lines, tissues, or pathological fluids from which the virus is cultured or obtained.

Vaccination can be conducted in conventional fashion. For example, the antigen, whether a viral particle or a protein, can be used in a suitable diluent such as water, saline, buffered salines, complete or incomplete adjuvants, and the like. The immunogen is administered using standard techniques for antibody induction, such as by subcutaneous administration of physiologically compatible, sterile solutions containing inactivated or attenuated virus particles or antigens. An immune response producing amount of virus particles is typically administered per vaccinizing injection, typically in a volume of one milliliter or less.

In addition to use as a vaccine, the compositions can be used to prepare antibodies to NANB virus particles. The antibodies can be used directly as antiviral agents. To prepare antibodies, a host animal is immunized using the virus particles or, as appropriate, non-particle antigens native to the virus particle are bound to a carrier as described above for vaccines. The host serum or plasma is collected following an appropriate time interval to provide a composition comprising antibodies reactive with the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other antiviral agents such as drugs.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas (see below).

The antibodies can also be used as a means of enhancing the immune response since antibody-virus complexes are recognized by macrophages. The anti-bodies can be administered in amounts similar to those used for other therapeutic administrations of anti-body. For example, pooled gamma globulin is administered at 0.02–0.1 ml/lb body weight during the early incubation of other viral diseases such as rabies, measles and hepatitis B to interfere with viral entry into cells. Thus, antibodies reactive with the NANB virus particle can be passively administered alone or in conjuction with another anti-viral agent to a host infected with a NANB virus to enhance the immune response and/or the effectiveness of an antiviral drug.

Alternatively, anti-NANB-virus antibodies can be induced by administering anti-idiotype antibodies as immunogens. Conveniently, a purified anti-NANB-virus antibody preparation prepared as descibed above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-NANB-virus antibodies, or by affinity chromatography using anti-NANB-virus antibodies bound to the affinity matrix. The anti-idiotype antibodies produced are similar in conformation to the authentic NANB antigen and may be used to prepare an NANB vaccine rather than using a NANB particle antigen.

When used as a means of inducing anti-NANB-virus antibodies in a patient, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable. The anti-idiotype method of induction of anti-NANB-virus antibodies can alleviate problems which may be caused by passive administration of anti-NANB-virus antibodies, such as an adverse immune response, and those associated with administration of purified blood components, such as infection with other as yet uncharacterized agents.

In addition to therapeutic uses, the particles and antigens of the invention, as well as the genetic material, can be used in diagnostic assays. Methods for detecting the presence of NANB hepatitis comprise analyzing a biological sample such as a blood sample or liver biopsy specimen for the presence of an analyte associated with NANB hepatitis virus. The analyte can be a nucleotide sequence which hybridizes with a probe comprising a sequence of at least about 16 consecutive nucleotides, usually 30 to 200 nucleotides, up to substantially the full sequence of the cDNA sequence shown in FIGS. 1 to 5. The analyte can be RNA or cDNA.

The analyte can be a virus particle having at least one of the following characteristics: obtainable from cells susceptible to infection with NANB hepatitis; capable of inducing expression of virus-specific surface antigen in a cell susceptible to infection by the particle, the surface antigen being recognized by serum from a host infected with NANB and not by serum from a non-infected host; having a buoyant density of from about 1.09 to 1.11 $gm/cm^2$. The virus particle can be further characterized as having an RNA viral genome comprising a sequence at least about 80% homologous to a sequence of at least 12 consecutive nucleotides of the sequences in FIGS. 1 to 5, usually at least about 90% homologous to at least about 60 consecutive nucleotides within the sequence, and may comprise a sequence substantially homologous to the sequences in FIGS. 1 to 5. The analyte can comprise an antibody which recognizes an antigen, such as a cell surface antigen, on a NANB virus particle. The analyte can also be a NANB viral antigen.

In order to detect an analyte, where the analyte hybridizes to a probe the probe may contain a detectable label. Likewise, where the analyte is an antibody or an antigen, either a labelled antigen or antibody, respectively, can be used to bind to the analyte to form an immunological complex, which can then be detected by means of the label.

Typically, methods for detecting analytes such as surface antigens and/or whole particles are based on immunoassays. Immunoassays can be conducted either to determine the presence of antibodies in the host that have arisen from infection by NANB hepatitis virus or by assays that directly determine the presence of virus particles or antigens. Such techniques are well known and need not be described here in detail. Examples include both heterogeneous and homogeneous immunoassay techniques. Both techniques are based on the formation of an immunological complex between the virus particle or its antigen and a corresponding specific antibody. Heterogeneous assays for viral antigens typically use a specific monoclonal or polyclonal antibody bound to a solid surface. Sandwich assays are becoming increasingly popular. Homogeneous assays, which are carried out in solution without the presence of a solid phase, can also be used, for example by determining the difference in enzyme activity brought on by binding of free antibody to an enzyme-antigen conjugate. A number of suitable assays are disclosed in U.S. Pat. Nos. 3,817,837, 4,006,360, 3,996,345.

When assaying for the presence of antibodies induced by NANB viruses, the viruses and antigens of the invention can be used as specific binding agents to detect either IgG or IgM antibodies. Since IgM anti-bodies are typically the first antibodies that appear during the course of an infection, when IgG synthesis may not yet have been initiated, specifically distinguishing between IgM and IgG antibodies present in the blood stream of a host will enable a physician or other investigator to determine whether the infection is recent or chronic.

The genetic material of the invention can itself be used in numerous assays as probes for genetic material present in naturally occurring infections. One method for amplification of target nucleic acids, for later analysis by hybridization assays, is known as the polymerase chain reaction or PCR technique. The PCR technique can be applied to detecting virus particles of the invention in suspected pathological samples using oligonucleotide primers spaced apart from each other and based on the genetic sequence set forth in FIGS. 1 to 5. The primers are complementary to opposite strands of a double stranded DNA molecule and are typically separated by from about 50 to 450 nt or more. This method entails preparing the specific oligonucleotide primers and then repeated cycles of target DNA denaturation, primer binding, and extension with a DNA polymerase to obtain probes of the desired length. Extension products generated from one primer serve as additional target sequences for the other primer. The degree of amplification of a target sequence is controlled by the number of cycles that are performed and is theoretically calculated by the simple formula $2^n$ where n is the number of cycles. Given that the average efficiency per cycle ranges from about 65% to 85%, 25 cycles produce from 0.3 to 4.8 million copies of the target sequence. The PCR method is described in a number of publications, including Saiki et al., *Science* (1985) 230:1350–1354; Saiki et al., *Nature* (1986) 324:163–166; and Scharf et al., *Science* (1986) 233:1076–1078. Also see U.S. Pat. Nos. 4,683,194; 4,683,195; and 4,683,202.

For both in vivo use of antibodies to NANB-virus particles and proteins and anti-idiotype anti-bodies and diagnostic use, it may be preferable to use monoclonal antibodies. Monoclonal anti-virus particle antibodies or anti-idiotype antibodies can be produced as follows. The spleen or lymphocytes from an immunized animal are removed and immortalized or used to prepare hybridomas by methods known to those skilled in the art. To produce a human-human hybridoma, a human lymphocyte donor is selected. A donor known to be infected with a NANB virus (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-virus particle antibodies, the antibodies must bind to NANB virus particles. For monoclonal anti-idiotype antibodies, the antibodies must bind to antivirus particle antibodies. Cells producing antibodies of the desired specificity are selected.

The invention now being generally described, the same will be better understood by reference to the following examples which are provided for purposes of illustration only and are not to be considered limiting of the invention unless so specified.

EXPERIMENTAL

Two hybrid liver cell cultures infected with NANB virus particles were deposited with the American Type Culture Collection (ATCC), 12301 Parklawn Drive, Rockville, Md. 20882, on Jun. 24, 1988. The two hybrid cultures are GLH03 and GLH04, and were given ATCC accession numbers CRL 9754 and CRL 9755, respectively. An uninfected hybrid liver-cell culture GLH02 was deposited with the ATCC on Mar. 26, 1986 and given ATCC accession number HB 9027.

EXAMPLE 1

Preparation of cDNA Clone from NANB Particles Isolated from Human Serum

Serum from human patients diagnosed as having NANB hepatitis was centrifuged at 30,000 rpm for 2½ hrs at 5° C. in an SW40 rotor (Beckman). The supernatant was removed and discarded and the pellet solubilized in 50 mM sodium acetate buffer, pH 4.8, containing 1% sodium dodecylsulfate (SDS). The RNA was selectively extracted using phenol equilibrated in the same buffer without SDS. The nucleic acid in the aqueous phase was then precipitated using two volumes of absolute ethanol. The RNA was reverse-transcribed into double-stranded cDNA using a DNA synthesis kit following the procedure specified by the manufacturer (Boehringer-Mannheim Biochemicals, Indianapolis, Ind.) except for the substitution of random primers for the oligo dt primer provided in the kit. The dsDNA obtained was ligated to EcoRI linkers and after generation of the cohesive EcoRI sites, was inserted into λgt11 as described by the supplier (ProMega Biotech, Madison, Wis.). The plaques were screened with NANB-infected human antisera and positive clones were isolated. The clones were then rescreened using the NANB-infected human antisera and plaque-purified.

Analysis of the sequences shown in FIGS. 1 to 4 using available sequence homology search programs revealed that the cloned sequences were unlike any entered in the data bank (GenBank versions 54 and 57). No homology was found to polypeptide sequences contained in GenBank version 52. Analysis of the DNA sequences shown in FIG. 5 (against GenBank version 57) showed no significant homology.

EXAMPLE 2

Purification of NANB Virus Particles From Infected Chimpanzee Plasma

NANB virus particles originally derived from human plasma were isolated as follows: A plasma inoculum from a chimpanzee inoculated with infected plasma comprising NANB virus particles originating from a patient diagnosed as having NANB hepatitis but carried in chimpanzees was layered onto the top of a linear 20-55% sucrose gradient in Tris HCl 0.01M, pH 8.0, containing 0.001M EDTA, 0.1M sodium chloride. The gradient was prepared using a Hoefer gradient maker. The chimpanzee inoculum contained $10^6$ chimpanzee infectious doses (CID) of NANB virus particles. The gradient was centrifuged for 18 hrs at 30,000 rpm at 5° C. in an SW40 rotor. Following fractionation of the gradient, the fractions were analyzed for infectivity by reinjection into chimpanzees. Fractions having a buoyant density of 1.09 to 1.11 gm/cm$^3$ were infectious at a dilution of 1:10$^6$, based upon alanine amino transferase (ALT) elevation at about 30 days postinoculation into the chimpanzee.

EXAMPLE 3

Preparation of cDNA from Purified Virus Particles

The virus particles obtained as described in Example 2, having a buoyant density of from 1.09 to 1.11 gm/cm$^3$ were used to prepare cDNA as described in Example 1. The cDNA obtained was then amplified using a technique described in co-owned patent application Ser. No. 208,512, filed Jun. 17, 1988, which disclosure is incorporated herein by reference. As a control, amplified cDNA was prepared from the buoyant density fractionated plasma of a chimpanzee chronically infected with HBV in the same manner as for the NANB cDNA. Infected and control amplified cDNAs were electrophoresized using an agarose gel (2%) and then transferred to nitrocellulose filters by the method of Southern (J. Mol. Biol. (1975) 98:503).

Clone #30 (obtained as in Example 1; sequence as in FIG. 1) was radiolabeled using $^{32}$P nucleotides and a random primer kit according to the instructions provided by the kit manufacturer (Boehringer-Mannheim Biochemicals, Indiannapolis, Ind.). The radio-labeled clone #30 was then used as a hybridization probe against a filter containing the amplified cDNAs from the fractionated virus particles. Specific hybridization, as detected by autoradiography, was evident only with the cDNA prepared from the NANB-infected chimpanzee. It was thus demonstrated that the molecular clone #30 isolated from a NANB-infected human source (identified by using serum from a different NANB-infected human and characterized as exogenous to the human and chimpanzee genomes) detected homologous sequences present in cDNA prepared from an enriched source of documented infectious NANB particles passaged in chimpanzees, but originating in an infected human. Clones PT'2, PT'8 and PT'9 also hybridized specifically to cDNA prepared from the NANB-infected chimpanzee.

EXAMPLE 4

Infection of Immortalized Liver Cells With NANB Virus

Hybrid liver cells were plated at $1 \times 10^6$ cells/well in a 24-well tray and overlaid with 100 ul of plasma from a chimpanzee known by its passage into a second chimpanzee to contain NANB viral agent(s); or (b) human plasma from an individual with acute posttransfusion NANB hepatitis. After an initial incubation of the chimpanzee serum and cells, 0.5 ml of growth medium containing IMDM and 20% FCS was added to each well and the cells were grown at 37° C. in a humidified 7% CO$_2$ incubator. The cultures were fed with growth medium every 3 to 4 days, and liver hybrid cells were removed every week to assay for the presence of NANB.

To detect the presence of virus particles, the cells were analysed for expression of NANB virus specific surface antigens. The method is as follows: An aliquot of the culture medium containing about $1 \times 10^7$ cells was removed from a culture well and the cells pelleted by centrifugation at 200×g for 10 minutes. After washing the cells three times with PBS, the cells were resuspended to $2.5 \times 10^6$ cells/ml and 10 ul of the cell suspension were dropped on a microscope slide and allowed to air-dry. The dried cells were then fixed on the slide by addition of acetone for one minute. To minimize non-specific binding, the slides were preincubated with normal goat serum (1:10 dilution) for 30 minutes at room temperature in a moist chamber. The slides were washed three times with PBS and once with distilled water, then 70 ul of test serum obtained from one of the panel chimpanzees (identified at the left in Table 2, see below) were added to the slides. Each serum sample had been preabsorbed with uninfected liver hybrid cells (10$^7$ cells per ml serum) to remove serum factors which tended to bind to the cells non-specifically. The slides containing the added serum were incubated in moist chambers for 90 minutes at room temperature, then again washed three times with PBS and once with distilled water.

Goat anti-human IgG and IgM conjugated with fluorescein isothiocyanate (FITC-conjugated antibody) were obtained from a commercial source (Zymed Labs). They were each diluted with PBS to a final concentration of about 1 ug antibody/ml. Either anti-IgM or anti-IgG FITC-conjugated antibody (70 ul) was added to the washed cells, and the slides were incubated at room temperature for 30 minutes. After washing with PBS and distilled water as above, the slides were mounted with one drop of 50% glycerol in PBS and observed under a fluorescence microscope. The cells were scored for weak (+), intermediate (++), and strong (+++) fluorescence.

The first indications of immunofluorescence occurred at about 6 to 8 weeks after initial cell infection with each virus source. The results shown in Table 2 were obtained 6 weeks post infection with chimpanzee plasma known to contain NANB agent(s).

TABLE 2

Expression of NANB Viral Cell Surface Antigens in Immortalized Liver Cells Infected witH NANB Virus

| Chimpanzee | Disease | Reactivity with Liver Hybridomas | |
|---|---|---|---|
| | | Infected | Uninfected |
| A | convalescent HAV | − | − |
| B[1] | normal | − | − |
| B | acute NANB | + | − |
| C | normal | − | − |
| D[1] | normal | − | − |
| D | acute NANB | ++ | − |
| E | normal | − | − |
| F | convalescent HBV | − | − |
| G | chronic NANB | +++ | − |
| H | chronic NANB | − | − |

[1]These animals are pre-NANB inoculation.

As seen in the right hand columns in Table 2, specific immunofluorescence was observed only with serum from NANB-infected animals, and not with serum from unifected animals or those infected with HBV. The results indicate that (a) the liver hybrid cells are infectable by NANB virus, (b) the infected hybrid cells are expressing a virus-specific surface antigen which is recognized by NANB serum antibody from chimps with known NANB infection, and (c) an incubation period of between about 4 to 6 weeks is required for surface antigen expression.

The results shown in Table 2 were obtained with anti-IgG antibody. No immunofluorescence was observed with FITC-conjugated anti-IgM antibody, as would be expected if the chimpanzee anti-NANB antibodies were IgG antibodies. Plasma from a patient with acute post-transfusion NANB gave a result similar to those obtained above with plasma from infected chimpanzees. After 6 weeks, liver hybrids infected using patient plasma showed specific immunofluorescence with serum from a NANB-infected chimpanzee, but not with control (uninfected) chimpanzee serum.

EXAMPLE 5

Recovery of NANB Infectious Virus Particles from Hybrid Liver Cells

The NANB-infected hybrid cells were also examined for the presence of infectious virus. Infected hybrid cells (obtained as described in Example 4) 12 weeks post infection were collected by centrifugation, then washed three times with PBS. The cells were resuspended in PBS to about $5 \times 10^6$ cells/ml and sonicated to clarity. The supernatants (0.5 ml/well) were then inoculated on uninfected hybrids and cultured in the manner described in Example 4 for cell infection by chimpanzee plasma. Cell-free lysates can also be prepared by hypotonic lysis or freeze-thawing. After about 6 to 8 weeks in continuous culture, specific immunofluorescence was observed with chimpanzee NANB serum, but not with serum from uninfected animals, demonstrating that the cell particles so propagated retained their infectivity.

EXAMPLE 6

Stability of Viral Infectivity of NANB Virus Particles Propagated in Hybrid Liver Cells Molecular clones from NANB-infected cells are isolated to determine if in vitro passage leads to the generation of defective viral particles, with resultant attenuation of viral infectivity. The method is as follows:

Infected cells are grown in exponential phase and then harvested by centrifugation for 10 minutes at 3,000 rpm. A cell-free lysate is prepared from $5 \times 10^8$ cells by 3 successive cycles of freezing on dry ice/ethanol and thawing at room temperature. The lysate is clarified by centrifugation at $10,000 \times g$ for 15 minutes in a microfuge. The supernatant is then loaded onto a linear sucrose density gradient as described above (see Example 2). The fractions having a buoyant density of from 1.09 to 1.11 gm/cm$^3$ are collected and particles extracted for RNA as described above in Example 3. After conversion to cDNA, and amplification as described in Example 3, the amplified cDNA is analysed by Southern blot hybridization to confirm the presence of NANB homologous sequences. The probes used are the cDNA clones whose sequence appears in FIGS. 1 to 4. The material is then cloned into λgt10 and molecular clones selected by hybridization using the molecular clones shown in FIGS. 1 to 4 as a probe. The primary nucleotide sequence of molecular clones derived from infected hybrid liver cells is then analysed to determine whether defective viral particles have been generated during passage in vitro.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A substantially pure polynucleotide having a region complementary to or the same as the entire of one of the following DNA sequences:

| 1 | ACACAACCAAATTCTTGGTTCCAGCGCCAA | |
|---|---|---|
| | CCTGAAACCAAA | 42 |
| 43 | AAAGTGGCAAATATTGCCGGGCAAGCGTCG | |
| | ATTGCTTCGACC | 84 |
| 85 | GCCTATGTGAGCCAAGATGCGGCCATTTCG | |
| | GCCTACAATAAA | 126 |
| 27 | GTAAAAAATGCTGTGGTCACCGTGCAAAAC | |
| | TTGCAAAAGAAT | 168 |
| 169 | GCGGCCCAAACCCCAGATGGTTTTGCGGGG | |
| | TTGTTTGGTCAA | 210 |
| 211 | TCAGGGCGTCAAAAGCAAGCCGATAATAAT | |

-continued

```
                                GGCCAAGTTGAA   252
253  ACTGCCTCAGAAGGCTCT                         270
``` or

```
  1  AAAAATAACAAGATCTTACATTTACGGAAA
                                TCTGCGACAAAA    42
 43  GTTTCCAAATATAAGATCAAAAAGTTAAGT
                                GTTGGTGTCGCC    84
 85  TCCGTTCTGGTGGGGGCCACTTTCTTCCTT
                                GGTTCGACAGCG   126
127  AGTGCAAGTGCTTCTGATGAGCAACTCGCT
                                GATAAGCAGGCA   168
169  GGGGTCACACAACAAACTGATCAAAATGCA
                                ACAAACACAAAT   210
211  GATCGGGTATTAAAGTTTGACAATGCAACG
                                TCAACGGCCACA   252
253  ACGGATAATGCTGATTCTAGTGCGGCCAAA
                                ATGTCAAACGTT   294
295  GCGCAAGCTGACAATTCAGCCAACAATGCA
                                ACAGTAGCTAAT   336
337  AATCTTGATAAAAAATCAATTACCGATTCT
                                ACATTATCCAAT   378
379  AATAACGATTTAAAATCAACTGAAATGCAA
                                TCAACTGTTACT   420
421  GACCAAGCAGCAGCTGACGATGCAAGTACT
                                GCTGATCAAACA   462
463  GCAACTGAAAAGCAAGCAACTGTGACCAAT
                                CAAGCCACAGTT   504
505  GATAACACAGTAAATACTGCTGACCAAGCA
                                ACTCAAGCAGCA   546
547  GCTGAAAAGACAACAACGCCTGCAAGTACT
                                GCTGCCAACACG   588
589  CAAGCAGCTGCACTAGTTGCAACGCTACGT
                                GCCGCAGCAACT   630
631  GCGGATACAAGTACGACGACAACTGTTAAC
                                AACTGGACT      669
``` or

```
  1  CCATCGGCTTCCATCCAGGAAGCAATGGAT
                                AAGCAGTTAACG    42
 43  GCTGATCGTGAACGAGTGGCAACTATTGCA
                                AAAGCCGAAGGG    84
 85  GAGGCACGCTCCATCGAACTCACAACCAAG
                                GCTAAAAATGAC   126
127  GCGTTGATGGCGACGGCGAAAGCCGAAGCT
                                GACGCGACGAAA   168
169  ACCCGTGCTGATGCCGAACGTTACCGAATC
                                GATACGGTACAA   210
211  GCTGGTTTGGCTGGGGCGGATGACAAGTAC
                                TTCCAAAACCAA   252
253  TCCATTAACGCATTCGCGACGTTACCCAAT
                                               282
``` or

```
                                ATCGAGAGCAACGCACTGGCAGTG
                                TCCAACCTGGATTTCTGATC
     CTGTTTTGACCCGCAGTACCCAAAAAGGCC
                                AACGCTCAGCGTTGGCCTTT
     TTTAATGGCTAAAAAATGACTATGGCGCCA
                                ACAGCACCGCCCTCTCCTCG
     CGGCACAACTCCAGTAAAAAATCCCACACC
                                ACCCTCAACCTTACGGATTT
                                GTGCAGTTCCCGGCGGGTGCTGATCCAGTA
                                ACTGCGTTGCACAGACTCGC
     CCGGCAATACACGCACCAGGTCGGGGTCGT
                                CAGCGGCCATGTAGTTGGGC
     AATACGGCGATACCCAGGCCGGCGCGAGCG
                                GCTTGTTGCTGGGCAATGAC
     GCTGGTGCTGCGAAAGGTCACGGTCGGGGT
                                GCGGCAGAAGGTATTGAGGA
     ACAGCAGCTCCTGACTGAACAACAGGTCGT
                                CGACGTAGCCGATCCAGTAG
     TGGTTGCCA
``` or

```
                                GTCATCACGCACA
                                ACAGGGGTGTTGAGCGGTGC
     ACCGAGTTCTTTCCAGTCCGGGAACAATTC
                                GTTCAGCGCACGGGGTTCAA
     ACACGGCACCGGACAGGATGTGAGCGCCGA
                                CTTCGGAGCCTTTTTCGACC
     ACGCAGACGCTGATTTCCTTACCGGCTTCG
                                GCGGCCTTCTGCTTCAATCG
     GCAGGCGGCAGACAGGCCTGCCGGGCCAGC
                                GCCGACGATGACCACGTC
``` or

```
                                GTTGACCACTC
```

-continued

```
          CCTGGCCGTCGAAGCCGGTG
GTTCGACCGACGCCTTCGAGAAGAACCGCG
          CCATCGAAGACCGCCGCAAC
GAAGACTGTTTCCACTTTATCGAGTGGACC
          AAAAAGGCCTTCAAGAACGT
CGATGTGATCCGCCGGGCAACGGCATCATG
          CACCAGATCAACCTGGAGAA
AATGTCGCCGGTGATCCAGGTGCGCGACGG
          CGTAGCTTCCGGATACCTGC
GTCGGCACCGATAGCCACACGCCCACGTGG
          ATGCCTTGGCGTGATCGCAT
CGGCTCTGGCGCGTA
or
          CCCCATAGAGCC
          CGGACCCATAGACAGCCCTG
CCCCATAGACAGTCTGGCCCTATAGACAGC
          CCAGCCCCATAGAGCCCGGC
CCTATAGATAGCCCGGCCCCATACAGCCCG
          GACCCATAGAGAGCACTGCC
CCATAGAGCCCGGACCCATAGAGCCCTGCC
          CCATAGACAGTC
or
          GCCAAAGAGTGG
          CGCACCGACCGTTCCCTCAG
CCGCCTCGAAGCCATGCTCGCCGTGGCCAA
          CAAAGACGCCTCCCTGATCA
TCACCGGCAACGGTGACGTGGTAGAGCCAG
          AAAACGGCTTGATCGCCATG
GGCTCCGGTGGCGGCTACGCCAGGCTGCGG
          CCAGTGCGCTGTTGAAGAAA
ACCGACCTGTCGGCCCGTGAAATCGTCGAG
          ACCGCCTTGGGCATCGCTGG
CGATATCTGCGTGTTCACCAACCACAACCT
          GACCATTGAGGAGCAGGACC
TCGCCGAGTAAGCCGTAGGCTTATTC
or
          GGCGATGACGG
          CTGCACCGCAAGCACCAGTA
```

-continued

```
TCAGTCCAGCCAAGTGAAACAGTGACACCT
          GCACAACCCGTCAAAGTTGC
ACCACAAGTGGTTGCAGCGCAACCAACGTC
          AACACCAACACCAACGGTAA
CAGTTGAGACTGTACCATCAACGCCTACGC
          CAGTGCCACCAACATTGGCA
ACGCCACCAATTGCACAACCAGTGGTAACT
          GCTGCGCCAACTGAAGAAGC
AGCCGTTGCCAACCAGTTGTGGGCACGTAC
          GGGACAAATGCGGTCTTTG
CCGTCCTACAACAAGCGAACGGAGACGCTT
          AGTCGCGTGAAGGCTGCTTG
GTCAGACTTGATTAGTCAATTTGGTGTTGC
          TGAACAGGCCTTACTGACGA
TTGCCGCCCCAGTAGCTGCAAGTGAGGAAG
          GGCTTGTTTTAGCGTTTGAT
TTTCCACCTTTATTGGCGCAAGCTTTACAA
          GATGCCGCCTTGCAAACGCA
ATTACGGACAGCGCTGGCTGCACAACAATT
          GCCAACAGAAATGGTGTTGA
TTACCCAAGATAGCTGGCAACAAGAACGCT
          CTGATTATGTCGCGCAGTTA
AAGGCGGGGACGACTCAACCTTTGAATTTG
          GCGGATATACCGAGAGTGAG
CCAAACAACCACGACCCAGTCGCAAAGTGC
          ACCGACACCAGAGCAAACGG
GGCTTG
or
TCGGGCCGGTAATGACCACGGCCAACCATAG
          CACCGCGAAGAAGCCTGCGA
TGGCGACGCTGGAGGCCATGGTGACGACGC
          TCCAATCGATGTCCGCGCGC
GCTCGGCGGCGCGATCTGCCGGATATCATC
          CGGCGCACCAGTCGGACGCC
GCAGCCGCGCTACCGGCCCGAGAAAGAAGA
          TCGCCGCCGCCCATTCGATG
GGGAACG.
```

2. The polynucleotide of claim 1 having a region complementary to or the same as the following DNA sequence:

```
 1  ACACAACCAAATTCTTGGTTCCAGCGCCAACCTGAAACCAAA  42
43  AAAGTGGCAAATATTGCCGGGCAAGCGTCGATTGCTTCGACC  84
```

```
 85 GCCTATGTGAGCCAAGATGCGGCCATTTCGGCCTACAATAAA    126
 27 GTAAAAAATGCTGTGGTCACCGTGCAAAACTTGCAAAAGAAT    168
169 GCGGCCCAAACCCCAGATGGTTTTGCGGGGTTGTTTGGTCAA    210
211 TCAGGGCGTCAAAAGCAAGCCGATAATAATGGCCAAGTTGAA    252
253 ACTGCCTCAGAAGGCTCT.                           270
```

3. The polynucleotide of claim 1 having a region complementary to or the same as the following DNA sequence:

```
  1 AAAAATAACAAGATCTTACATTTACGGAAATCTGCGACAAAA    42
 43 GTTTCCAAATATAAGATCAAAAAGTTAAGTGTTGGTGTCGCC    84
 85 TCCGTTCTGGTGGGGGCCACTTTCTTCCTTGGTTCGACAGCG    126
127 AGTGCAAGTGCTTCTGATGAGCAACTCGCTGATAAGCAGGCA    168
169 GGGGTCACACAACAAACTGATCAAAATGCAACAAACACAAAT    210
211 GATCGGGTATTAAAGTTTGACAATGCAACGTCAACGGCCACA    252
253 ACGGATAATGCTGATTCTAGTGCGGCCAAAATGTCAAACGTT    294
295 GCGCAAGCTGACAATTCAGCCAACAATGCAACAGTAGCTAAT    336
337 AATCTTGATAAAAAATCAATTACCGATTCTACATTATCCAAT    378
379 AATAACGATTTAAAATCAACTGAAATGCAATCAACTGTTACT    420
421 GACCAAGCAGCAGCTGACGATGCAAGTACTGCTGATCAAACA    462
463 GCAACTGAAAAGCAAGCAACTGTGACCAATCAAGCCACAGTT    504
505 GATAACACAGTAAATACTGCTGACCAAGCAACTCAAGCAGCA    546
547 GCTGAAAAGACAACAACGCCTGCAAGTACTGCTGCCAACACG    588
589 CAAGCAGCTGCACTAGTTGCAACGCTACGTGCCGCAGCAACT    630
631 GCGGATACAAGTACGACGACAACTGTTAACAACTGGACT.      669
```

4. The polynucleotide of claim 1 having a region complementary to or the same as the following DNA sequence:

```
  1 CCATCGGCTTCCATCCAGGAAGCAATGGATAAGCAGTTAACG    42
 43 GCTGATCGTGAACGAGTGGCAACTATTGCAAAAGCCGAAGGG    84
 85 GAGGCACGCTCCATCGAACTCACAACCAAGGCTAAAAATGAC    126
127 GCGTTGATGGCGACGGCGAAAGCCGAAGCTGACGCGACGAAA    168
169 ACCCGTGCTGATGCCGAACGTTACCGAATCGATACGGTACAA    210
211 GCTGGTTTGGCTGGGGCGGATGACAAGTACTTCCAAAACCAA    252
253 TCCATTAACGCATTCGCGACGTTACCCAAT.               282
```

5. The polynucleotide of claim 1 having a region complementary to or the same as the following DNA sequence:

```
ATCGAGAGCAACGCACTGGCAGTGTCCAACCTGGATTTCTGATC
CTGTTTTGACCCGCAGTACCCAAAAAGGCCAACGCTCAGCGTTGGCCTTT
TTTAATGGCTAAAAAATGACTATGGCGCCAACAGCACCGCCCTCTCCTCG
CGGCACAACTCCAGTAAAAAATCCCACACCACCCTCAACCTTACGGATTT
GTGCAGTTCCCGGCGGGTGCTGATCCAGTAACTGCGTTGCACAGACTCGC
CCGGCAATACACGCACCAGGTCGGGGTCGTCAGCGGCCATGTAGTTGGGC
```

-continued

AATACGGCGATACCCAGGCCGGCGCGAGCGGCTTGTTGCTGGGCAATGAC

GCTGGTGCTGCGAAAGGTCACGGTCGGGGTGCGGCAGAAGGTATTGAGGA

ACAGCAGCTCCTGACTGAACAACAGGTCGTCGACGTAGCCGATCCAGTAG

TGGTTGCCA.

6. The polynucleotide of claim 1 having a region complementary to or the same as the following DNA sequence:

GTCATCACGCACAACAGGGGTGTTGAGCGGTGC

ACCGAGTTCTTTCCAGTCCGGGAACAATTCGTTCAGCGCACGGGGTTCAA

ACACGGCACCGGACAGGATGTGAGCGCCGACTTCGGAGCCTTTTTCGACC

ACGCAGACGCTGATTTCCTTACCGGCTTCGGCGGCCTTCTGCTTCAATCG

GCAGGCGGCAGACAGGCCTGCCGGGCCAGCGCCGACGATGACCACGTC.

7. The polynucleotide of claim 1 having a region complementary to or the same as the following DNA sequence:

GTTGACCACTCCCTGGCCGTCGAAGCCGGTG

GTTCGACCGACGCCTTCGAGAAGAACCGCGCCATCGAAGACCGCCGCAAC

GAAGACTGTTTCCACTTTATCGAGTGGACCAAAAAGGCCTTCAAGAACGT

CGATGTGATCCGCCGGGCAACGGCATCATGCACCAGATCAACCTGGAGAA

AATGTCGCCGGTGATCCAGGTGCGCGACGGCGTAGCTTCCGGATACCTGC

GTCGGCACCGATAGCCACACGCCCACGTGGATGCCTTGGCGTGATCGCAT

CGGCTCTGGCGCGTA.

8. The polynucleotide of claim 1 having a region complementary to or the same as the following DNA sequence:

CCCCATAGAGCCCGGACCCATAGACAGCCCTG

CCCCATAGACAGTCTGGCCCTATAGACAGCCCAGCCCCATAGAGCCCGGC

CCTATAGATAGCCCGGCCCCATACAGCCCGGACCCATAGAGAGCACTGCC

CCATAGAGCCCGGACCCATAGAGCCCTGCCCCATAGACAGTC.

9. The polynucleotide of claim 1 having a region complementary to or the same as the following DNA sequence:

GCCAAAGAGTGGCGCACCGACCGTTCCCTCAG

CCGCCTCGAAGCCATGCTCGCCGTGGCCAACAAAGACGCCTCCCTGATCA

TCACCGGCAACGGTGACGTGGTAGAGCCAGAAAACGGCTTGATCGCCATG

GGCTCCGGTGGCGGCTACGCCAGGCTGCGGCCAGTGCGCTGTTGAAGAAA

ACCGACCTGTCGGCCCGTGAAATCGTCGAGACCGCCTTGGGCATCGCTGG

CGATATCTGCGTGTTCACCAACCACAACCTGACCATTGAGGAGCAGGACC

TCGCCGAGTAAGCCGTAGGCTTATTC.

10. The polynucleotide of claim 1 having a region complementary to or the same as the following DNA sequence:

GGCGATGACGGCTGCACCGCAAGCACCAGTA

TCAGTCCAGCCAAGTGAAACAGTGACACCTGCACAACCCGTCAAAGTTGC

ACCACAAGTGGTTGCAGCGCAACCAACGTCAACACCAACACCAACGGTAA

CAGTTGAGACTGTACCATCAACGCCTACGCCAGTGCCACCAACATTGGCA

-continued

```
ACGCCACCAATTGCACAACCAGTGGTAACTGCTGCGCCAACTGAAGAAGC
AGCCGTTGCCAACCAGTTGTGGGCACGTACGGGACAAAATGCGGTCTTTG
CCGTCCTACAACAAGCGAACGGAGACGCTTAGTCGCGTGAAGGCTGCTTG
GTCAGACTTGATTAGTCAATTTGGTGTTGCTGAACAGGCCTTACTGACGA
TTGCCGCCCCAGTAGCTGCAAGTGAGGAAGGGCTTGTTTTAGCGTTTGAT
TTTCCACCTTTATTGGCGCAAGCTTTACAAGATGCCGCCTTGCAAACGCA
ATTACGGACAGCGCTGGCTGCACAACAATTGCCAACAGAAATGGTGTTGA
TTACCCAAGATAGCTGGCAACAAGAACGCTCTGATTATGTCGCGCAGTTA
AAGGCGGGGACGACTCAACCTTTGAATTTGGCGGATATACCGAGAGTGAG
CCAAACAACCACGACCCAGTCGCAAAGTGCACCGACACCAGAGCAAACGG
GGCTTG.
```

11. The polynucleotide of claim 1 having a region complementary to or the same as the following DNA sequence:

```
TCGGGCCGGTAATGACCACGGCCACCATAGCACCGCGAAGAAGCCTGCGA
TGGCGACGCTGGAGGCCATGGTGACGACGCTCCAATCGATGTCCGCGCGC
GCTCGGCGGCGCGATCTGCCGGATATCATCCGGCGCACCAGTCGGACGCC
GCAGCCGCGCTACCGGCCCGAGAAAGAAGATCGCCGCCGCCCATTCGATG
GGGAACG.
```

* * * * *